(12) United States Patent
Tsuyama et al.

(10) Patent No.: US 12,198,811 B2
(45) Date of Patent: Jan. 14, 2025

(54) PATHOLOGY IMAGE MANAGEMENT SYSTEM

(71) Applicants: JAPANESE FOUNDATION FOR CANCER RESEARCH, Tokyo (JP); KONINKLIJKE PHILIPS N.V., Eindhoven (NL); FINGGAL LINK CO., LTD., Tokyo (JP)

(72) Inventors: Naoko Tsuyama, Tokyo (JP); Kengo Takeuchi, Tokyo (JP); Sayuri Nakamura, Tokyo (JP); Masayuki Hayashi, Tokyo (JP); Takuya Sato, Tokyo (JP)

(73) Assignees: KONINKLIJKE PHILIPS N.V., Eindhoven (NL); FINGGAL LINK CO., LTD, Tokyo (JP); JAPANESE FOUNDATION FOR CANCER RESEARCH, Tokyo (JP)

( * ) Notice: Subject to any disclaimer, the term of this patent is extended or adjusted under 35 U.S.C. 154(b) by 428 days.

(21) Appl. No.: 17/639,062

(22) PCT Filed: Aug. 27, 2020

(86) PCT No.: PCT/JP2020/032318
§ 371 (c)(1),
(2) Date: Feb. 28, 2022

(87) PCT Pub. No.: WO2021/039889
PCT Pub. Date: Mar. 4, 2021

(65) Prior Publication Data
US 2022/0384037 A1 Dec. 1, 2022

(30) Foreign Application Priority Data
Aug. 28, 2019 (JP) .................. 2019-155789

(51) Int. Cl.
G16H 50/20 (2018.01)
G16H 10/40 (2018.01)
(Continued)

(52) U.S. Cl.
CPC ............. *G16H 50/20* (2018.01); *G16H 10/40* (2018.01); *G16H 15/00* (2018.01); *G16H 30/20* (2018.01);
(Continued)

(58) Field of Classification Search
CPC ........ G16H 50/20; G16H 10/40; G16H 15/00; G16H 30/20; G16H 30/40; G16H 70/60; G16H 30/00; G06T 1/00; G02B 21/34
(Continued)

(56) References Cited

U.S. PATENT DOCUMENTS

2002/0019854 A1  2/2002 Sagi
2003/0177041 A1  9/2003 Millican et al.
(Continued)

FOREIGN PATENT DOCUMENTS

JP  2013-054083  3/2013
JP  2013-539097  10/2013
(Continued)

OTHER PUBLICATIONS

English translation of Written Opinion of the International Searching Authority dated Nov. 20, 2020, Application No. PCT/JP2020/032318, 3 pages.

*Primary Examiner* — Juan A Torres
(74) *Attorney, Agent, or Firm* — Sherry Austin

(57) ABSTRACT

A laboratory information system (LIS) is linked with a whole slide image (WSI) management system to build a pathology image management system that can efficiently manage and utilize a digitized pathology image. A scan notification notifying that an image of a glass slide is
(Continued)

scanned by a scanner is delivered to the LIS from the WSI management system to form a WSI link in the LIS, so that the LIS is linked with the WSI management system. By linking two systems with each other can eliminate the problem of mixing up specimens, for example, and hence, a pathologist can easily grasp the status of a pathology sample for which the pathologist is responsible.

13 Claims, 7 Drawing Sheets

(51) Int. Cl.
    *G16H 15/00*     (2018.01)
    *G16H 30/20*     (2018.01)
    *G16H 30/40*     (2018.01)
    *G16H 70/60*     (2018.01)
    *G06T 1/00*     (2006.01)

(52) U.S. Cl.
    CPC ............ *G16H 30/40* (2018.01); *G16H 70/60* (2018.01); *G06T 1/00* (2013.01)

(58) Field of Classification Search
    USPC ....................................................... 382/128
    See application file for complete search history.

(56) References Cited

U.S. PATENT DOCUMENTS

| | | |
|---|---|---|
| 2008/0086335 A1 | 4/2008 | Matsue et al. |
| 2008/0247676 A1 | 10/2008 | Minakuchi et al. |
| 2009/0087048 A1 | 4/2009 | Takahashi |
| 2011/0022658 A1 | 1/2011 | Pace et al. |
| 2011/0052017 A1* | 3/2011 | Suwaki .................. G16H 40/20 382/128 |
| 2011/0060766 A1 | 3/2011 | Ehlke et al. |
| 2011/0274320 A1 | 11/2011 | Pace et al. |
| 2015/0169555 A1 | 6/2015 | Wrenn et al. |
| 2015/0279026 A1 | 10/2015 | Hall et al. |
| 2018/0018426 A1* | 1/2018 | Hwang .................. G06T 7/0012 |
| 2018/0226138 A1* | 8/2018 | Leavitt .................. G16H 50/20 |
| 2018/0239867 A1 | 8/2018 | Kopylov |
| 2018/0340870 A1 | 11/2018 | Gustafson et al. |
| 2022/0005582 A1* | 1/2022 | Linhart .................. G16H 10/40 |

FOREIGN PATENT DOCUMENTS

| | | |
|---|---|---|
| JP | 2015-533232 | 11/2015 |
| WO | 2014/018114 | 1/2014 |

* cited by examiner

PATHOLOGY IMAGE MANAGEMENT SYSTEM

TECHNICAL FIELD

The present invention relates to a method and a system for managing and utilizing medical data by using digital techniques. The present invention particularly relates to a method for managing and utilizing medical data in pathological diagnosis that uses a whole slide image (hereinafter, referred to as "WSI").

BACKGROUND ART

In recent years, there has been a progress in technological advancements, such as digital health and smart health, where IT technology is used in the field of healthcare relating to health, medical care, and nursing care. Also in the field of pathological diagnosis, digital pathology has begun to be adopted, where a glass slide (pathological tissue sample) is digitized and displayed on a display for observation. This digital pathology has brought about a significant revolution in pathological diagnosis.

Digital pathology is one field of pathology and is being developed to study a large amount of image-based information generated from forming digital images out of samples on a slide glass. In recent years, a technique has been introduced where a glass slide is scanned by using a dedicated scanner, and is treated as one image file obtained by connecting images, that is, as a WSI. Therefore, rapid progress has been achieved in digital pathology where WSI is managed and analyzed together with various kinds of information and is applied to remote diagnosis and diagnostic assistance for a pathologist, or to analytical study of biomarkers, for example. Further, in December 2017, a pathology whole slide image diagnosis assisting device made by Royal Philips has been granted pharmaceutical approval for the first time in Japan as medical equipment used for the purpose of assisting a pathological diagnosis by using digital images, thus bringing about a significant revolution in pathology and pathological diagnosis.

Digitization of a pathology image is a technique that enables the pathology image to be observed on the display of a PC, and such a technique enables various activities that have been difficult to achieve. For example, such a technique allows a plurality of pathologists to share the same information only with the Internet environment, thus enabling the pathologists to have a joint conference to give consideration to a case even when the pathologists are remote from each other. Further, annotation can be applied to an image and hence, the basis for a diagnosis or the like can be accurately communicated with each other. As a result, such a technique is used not only for assisting remote pathological diagnosis but also for pathologist training. When a plurality of pathologists can share a digital image as described above, it is unnecessary to prepare a plurality of glass slides and hence, the load on a pathology department is reduced.

On the other hand, when a pathologist makes pathological diagnosis by using WSI on a clinical site, it is necessary to link a WSI management system with electronic medical records and a laboratory information system (hereinafter referred to as "LIS"), which are existing systems used in a hospital or the like. Patent Literature 1 discloses the invention of a system that performs package processing on WSI data and patient data, which are extracted from the LIS, to compress and distribute the data. However, in this method, an existing LIS and existing electronic medical records are not linked with a WSI management system and hence, this method fails to achieve a system that combines with existing systems to allow pathologists to efficiently diagnose a processed image.

CITATION LIST

Patent Literature

Patent Literature 1: Japanese Translation of PCT International Application Publication No. 2013-539097

SUMMARY OF INVENTION

Technical Problem

A pathologist uses a WSI viewer to view a WSI, and uses the LIS to make a diagnosis report or to give an order for a test. However, at present, each of the WSI management system, including the viewer, and the LIS is operated as an independent system and hence, specimen information is not integrated, thus causing a problem of mixing up specimens or a problem in work efficiency, for example. For this reason, there is a demand for improvement.

For example, a pathology number is assigned to each pathological specimen and is assigned by the LIS linked with the electronic medical record, but is not linked with the WSI management system. Therefore, it is necessary to apply specimen information to WSI data, which is obtained by the scanner, by inputting a pathology number and staining information with the WSI management system. Further, in viewing a WSI, the corresponding pathology number is inputted into a search field of the viewer to search for and view a file. However, at the time of performing such operations, input error may occur, thus causing the problem of mixing up specimens.

When the WSI management system is set to be associated with a pathology number, made by the LIS, to solve such a problem, such setting allows a linkage, where a WSI link of the corresponding case can be opened with the diagnosis screen of the LIS being in an open state, thus eliminating the labor of inputting a search key and the problem of mixing up specimens caused by input error. A method frequently used is that, with the diagnosis screen of the LIS being in an open state, the WSI link is clicked to display WSI via a browser in the same manner as viewing a macro image. If a diagnosis list for each pathologist is made on the LIS, the pathologist can start a diagnosis without a request or glass slides. However, in the case of this method, when a browser is not closed each time a case is changed in the LIS, a state is brought about where WSI of different cases can be viewed simultaneously in a plurality of tabs. Therefore, the risk of mixing up specimens remains. Further, although this method is specialized in the function of displaying WSI based on a pathology number, this method is not sufficient to promote management of WSI and entering pathology information into a database. In other words, it is difficult to say that this system is sufficient to view, search, and classify a saved WSI. Further, a scan completion notification is not linked and hence, a pathologist cannot obtain information from the LIS, such as whether all images necessary for a diagnosis have been imported or when the pathologist can start a diagnosis, for example.

A conventional method for making a pathological diagnosis will be outlined to describe the problems in a conventional method. Even before the introduction of WSI, in a network system that manages medical information in a hospital, electronic medical records are linked with an LIS to exchange information between a clinical department and the pathology department (FIG. 6). In the pathology department, a test or a diagnosis is started with a request for a pathological diagnosis, which is made through an electronic medical record by a doctor in the clinical department, such as a surgeon. The pathology department accepts a specimen submitted together with the order for a pathological diagnosis request obtained through the electronic medical record, and issues one pathology number for one specimen. In the pathology department, the specimen is excised and an order for required staining for each specimen is given through the LIS to prepare a glass slide. Before a pathology image is digitized, a pathologist observes a sample of glass slide through a microscope, makes a diagnosis report based on resulting findings, and inputs the diagnosis report into the LIS. Since the electronic medical record is linked with the LIS, the diagnosis report which is made can be viewed on the electronic medical record, thus allowing the clinician who made the request for a pathological test to decide a treatment policy for the patient while referring to the diagnosis report. Although the electronic medical record system is linked with the LIS, each of the electronic medical record system and the LIS is operated by own system, and respective data are saved in different databases (DBs). Accordingly, in the case where a clinician desires to confirm information that is not described in the report from a pathology image, it is necessary for the clinician to request the pathology department to evaluate again or it is necessary for the clinician to directly observe the glass slide through a microscope in the pathology department.

Even after the introduction of the WSI, at present, the linkage of the WSI with a medical information management network, such as the existing LIS and the existing electronic medical record system, is unfortunately insufficient (FIG. 7). In the clinical department, an order for a pathological diagnosis request is issued through the electronic medical record and a specimen is submitted to the pathology department in the same manner as before the introduction of the WSI. In the pathology department, after the acceptance of the specimen, issuance of a pathology number and an order for required staining are made through the LIS. A glass slide is subject to required steps, such as sectioning and staining, and is then read by the scanner. WSI data read by the scanner is transferred to the WSI management system. However, the WSI management system is not linked with the LIS and hence, a pathology number is not assigned to the image read by the scanner. Therefore, the pathology number is manually inputted in the WSI management system to cause image data to be associated with the pathology number.

A pathologist makes a diagnosis by viewing the image, to which the pathology number is assigned, through the WSI management system. In making a diagnosis, only information on the scanned image can be obtained from the WSI management system and hence, it is necessary for the pathologist to obtain information on other specimen and patient information through the LIS, which is linked with the electronic medical record, or directly from the electronic medical record. After the pathologist makes a diagnosis report and inputs the diagnosis report into the LIS, a clinician can decide a treatment policy for the patient by referring to the diagnosis report, which is stored in the LIS, through the electronic medical record.

As described above, conventionally, although the electronic medical record system is linked with the LIS, the WSI management system is not linked with any system. Therefore, it is necessary to assign a pathology number to an image, which is read by the scanner, by manually inputting the pathology number and hence, a human error may occur, such as an error in inputting the pathology number. Further, in making a diagnosis report, it is necessary to call an image from the WSI management system and to call patient information from the LIS to make a diagnosis and hence, it takes time to separately access two different systems. Further, when the clinician who reads the diagnosis report desires to view an image that is not attached to the diagnosis report, since the WSI management system is not linked with the LIS, it is necessary to further request the pathology department to send the image data. The introduction of the WSI allows pathology images to be obtained as digital images, thus bringing about a significant innovation in pathological diagnosis. However, further improvement is necessary from a viewpoint of improving efficiency in pathological diagnosis.

For a long period of time, pathologists have been familiar with conventional systems, such as a microscope, an electronic medical record system, and the LIS and have performed diagnostic work ranging from the receiving an order for a pathological diagnosis to making a report based on the LIS being partially linked with an electronic medical record system which is built.

A pathologist treats information for each individual case as one package, that is, as a so-called "case file". In other words, the pathologist treats not only pathology images but also any information necessary for a pathological diagnosis as one case file to make a diagnosis. Specific examples of information necessary for a pathological diagnosis include clinical information for the patient, test data, radiographic images, presented information on management of steps for a pathology sample, and the like. The work of the pathologists is to process a large number of case files. In pathological diagnosis sites, the pathologists are familiar with and accustomed to handling conventionally used tools, such as a microscope system, the electronic medical record system, and the LIS. Therefore, there is a demand to build a digital pathology system that imitates the experience of using the conventionally used tools in making a pathological diagnosis by using pathology image data, which are digitized into case information that is treated as such a case file. There is also a demand to build a system with functions that have been difficult to be achieved, such as functions for sharing information with others, for searching, and for classifying data.

It is an object of the present invention to build a system that allows a pathologist to efficiently access the LIS to perform work while viewing and managing a WSI. It is also an object of the present invention to build a system that allows a pathologist to grasp the amount of work, to confirm the state of a diagnosis progress, and to manage images in a daily workflow.

Solution to Problem

The present invention relates to the following system.

(1) A pathology image management system that controls linkage among a scanner, a whole slide image (WSI) management system, and a laboratory information system (LIS), the scanner scanning a glass slide to digitize the glass slide, wherein WSI data obtained by the scanner are transferred to the WSI management system, the WSI management system delivers a scan notification to the LIS, the scan notification notifying that the WSI data is transferred, and a WSI link is formed in the LIS that receives the scan notification.

(2) The pathology image management system according to (1), wherein
the WSI management system includes
a currently-being-prepared folder that stores information on the glass slide up to a point before formation of the WSI link,
a currently-in-diagnosis folder that stores the WSI data in a state where viewing of an image is allowed, and
a completed folder that stores the WSI data for which a report is made.

(3) The pathology image management system according to (1) or (2), wherein
the WSI data in which the WSI link is formed
are saved in a case file folder for every one specimen, and
are stored in a folder in the WSI management system.

(4) The pathology image management system according to (2) or (3), wherein
the WSI management system further includes an additional-staining currently-in-request folder.

(5) The pathology image management system according to any one of (2) to (4), wherein
upon acceptance of a specimen, the LIS issues a pathology number,
the pathology number issued is stored in the currently-being-prepared folder of the WSI management system, and
the pathology number issued is printed on the glass slide or is stuck to the glass slide in a form of a label,
the scanner simultaneously reads the WSI data and the pathology number printed or stuck in the form of the label to cause the pathology number to be associated with the WSI data, and
the pathology number and the WSI data are stored in the currently-being-prepared folder of the WSI management system.

(6) The pathology image management system according to any one of (2) to (5), wherein
a link is formed for WSI in response to scan notification, after the LIS confirms completion of scanning for each of all glass slides for which an order is made,
a case file folder is moved from the currently-being-prepared folder and is stored in the currently-in-diagnosis folder, and
a scan completion notification is sent to a responsible doctor.

(7) The pathology image management system according to any one of (2) to (6), wherein
upon determination of necessity of additional staining,
an order for the additional staining is given to the LIS, so that an additional stain slide label is issued or the pathology number is printed on the glass slide,
the scanner obtains an image of the glass slide on which required staining is performed,
WSI data on the glass slide on which the additional staining is performed are transferred to the WSI management system, the WSI data being obtained by the scanner,
the WSI management system delivers, to the LIS, the scan notification notifying that the WSI data are transferred, and
a WSI link of an additional staining image is formed in the LIS that receives the scan notification.

(8) The pathology image management system according to any one of (2) to (7), wherein
after a diagnosis report is made in the LIS,
the WSI data are moved from the currently-in-diagnosis folder and are stored in the completed folder.

(9) The pathology image management system according to any one of (1) to (8), wherein a tag applied through the LIS is displayed on a terminal for a responsible pathologist, the tag showing a priority order of diagnosis.

(10) The pathology image management system according to any one of (1) to (9), wherein application of an arbitrary tag is allowed to be applied by a terminal for a responsible pathologist.

(11) The pathology image management system according to any one of (2) to (10), comprising an archive storage for storing data, wherein
the pathology image management system is built such that a case file folder stored in the completed folder is automatically moved to the archive storage after a lapse of a predetermined period of time.

(12) The pathology image management system according to (11), wherein in a case where a specimen that is newly accepted has a past sample,
the LIS detects presence of the past sample, and
retrieving of the past sample from the archive storage is demanded, and the past sample is automatically retrieved.

(13) The pathology image management system according to (11) or (12), wherein a tag is applied to the case file folder that is retrieved from the archive storage, and
the case file folder is stored in the archive storage again after a lapse of a predetermined period of time.

DESCRIPTION OF EMBODIMENT

Methods described in the following embodiments are methods and systems that cause an existing LIS to be efficiently linked with a WSI management system. Examples of the LIS include PATH Dimension (FINGGAL LINK CO., LTD.), CLINILAN WebPath (A&T Corporation), EXpath (INTEC Inc.), Dr. Helper (Mighty Net Co., Ltd.), Path Window (Matsunami Glass Ind., Ltd.), PathoTopia (MUTO PURE CHEMICALS CO., LTD.), WebPath (Medical Systems Co., Ltd.), and CNA-Net pathology (Sakura Finetek Japan Co., Ltd.). Examples of the WSI management system include image management system (Royal Philips), Aperio eSlide Manager (Leica Biosystems), and CaseCenter (3DHISTECH). Examples of a scanner that digitizes a glass slide include Ultra Fast Scanner (Royal Philips), NanoZoomer (HAMAMATSU PHOTONICS K.K.), Aperio (Leica Biosystems), Pannoramic Digital Slide Scanners (3DHISTECH), MoticEasyScan (Motic), VS120 (Olympus), VENTANA iScan (Roche Diagnostics), and MIRAX SCAN (Zeiss). In the embodiments, PATH Dimension is used as the LIS, image management system is used as the WSI management system, and Ultra Fast Scanner is used as the scanner. However, it is needless to say that any system or equipment can build the pathology image management system shown in the embodiment.

Embodiment 1

Figure 1:
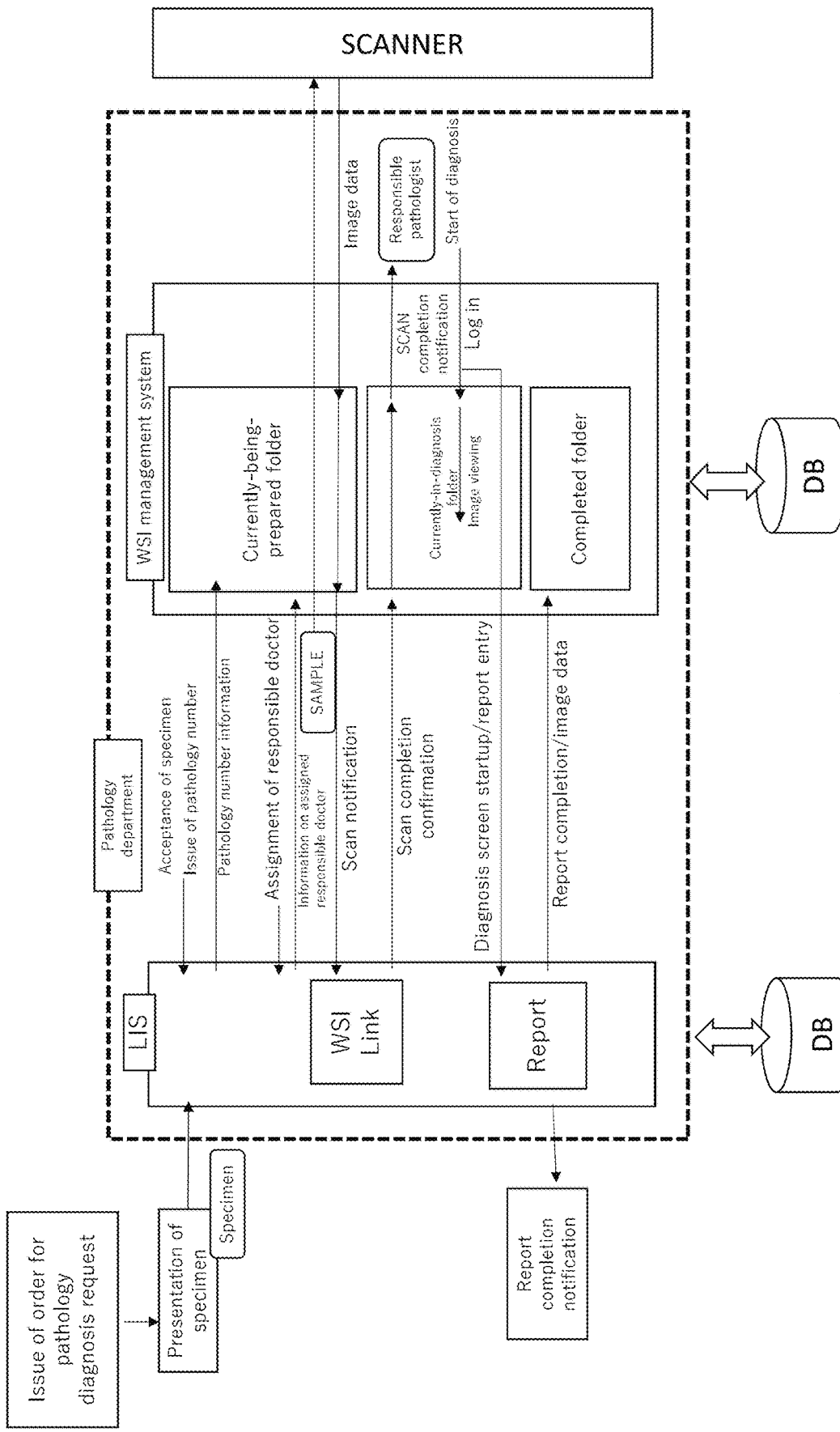
FIG. 1 is a diagram schematically showing a pathology image management system.

An Embodiment of the present invention will be described (a clinical department and a linkage between an electronic medical record system and an LIS are substantially equal to those in the conventional method, thus being omitted from FIG. 1). Also in the system of this embodiment, a pathological diagnosis is requested and a specimen is submitted from the clinical department, and a pathology number is issued in a pathology department in the same manner. In other words, an order for pathological diagnosis request is issued in the clinical department, arrival of the submitted specimen at the pathology department is confirmed, and the submitted specimen is accepted. When the sample is accepted, each sample is classified according to whether the sample includes a biopsy specimen, a surgical specimen, or a specimen requiring an urgent diagnosis and according to whether the sample is an outside-hospital sample that is sent from another hospital with a request for diagnosis, for example. Thereafter, a pathology number is issued. The issued pathology number is printed on or stuck to a glass slide in the form of a label, and a case file folder to which pathology number information is applied is stored in a currently-being-prepared folder of the WSI management system.

Assignment of responsible pathologists for respective specimens is inputted into the LIS. Alternatively, in the case where specialties of a plurality of pathologists are clear, it is also possible to automatically assign a specimen based on the field of specialty at the point in time when a pathology number is assigned to the specimen. Information on the assigned responsible doctors is delivered from the LIS to the case file folder stored in the currently-being-prepared folder of the WSI management system. The assignment of responsible pathologists may be performed at any step of the process ranging from issuing of a pathology number to the completion of a diagnosis.

A specimen passes through required steps, such as cutting, decalcification, embedding, sectioning, and staining, to prepare a glass slide. When the stained-glass slide is set on a scanner, which is connected with the WSI management system, reading of an image is started. The scanner also reads a label portion on the glass slide simultaneously when the scanner reads the image, so that the pathology number assigned by the LIS is associated with a WSI. Specifically, it is sufficient to adopt the following configuration. Specimen information (pathology number, sample block number, kind of staining and the like) of an individual glass slide is printed on the label portion of the glass slide in the form of a barcode or a QR code (registered trademark). The scanner also reads the barcode or the like simultaneously when reading the image, and the obtained image is associated with the pathology number. Specimen information including the pathology number is associated with image data simultaneously with the reading of the image and hence, it is possible to avoid human errors which have not been eliminated, such as an input error in a pathology number or mixing up glass slides.

The image data read by the scanner is stored in the currently-being-prepared folder and the LIS is notified of a fact that the image is scanned (scan notification). When the LIS receives the scan notification, a WSI link is formed. There may be a case where one glass slide (slide) is prepared from one specimen. However, usually, a plurality of glass slides is prepared from one specimen. For each of all glass slides of one specimen for which an order is made, a WSI link is formed in the LIS. In other words, when a state is brought about where a diagnosis can be started, scan completion confirmation is delivered to the WSI management system, and the case file folder is moved from the currently-being-prepared folder and is stored in a currently-in-diagnosis folder. When the case file folder is stored in the currently-in-diagnosis folder, a scan completion notification is delivered to a terminal for a responsible pathologist. When the responsible pathologist receives the scan completion notification, the responsible pathologist can confirm that a diagnosis can be started.

Logging in the WSI management system allows the pathologist to access image data on a list of case file folders to which the pathologist is assigned to make a diagnosis. The case file folder indicates a folder in which images of each specimen (each pathology number) are stored, and the responsible doctor can start a diagnosis by accessing the case file folder to which the doctor is assigned. At this point of operation, only a WSI transferred from the scanner is stored in the case file folder. However, the case file folder may also store other modality images and the like which are necessary for a diagnosis when necessary, such as macro images, PDF documents, such as a genetic test result report, or images imported from an electronic medical record.

Simultaneously with the selection of the case file folder on the WSI management system by the pathologist, the LIS starts up and a diagnosis screen for the case that matches the pathology number in the case file folder is automatically called on the LIS. Accordingly, the pathologist can obtain diagnosis information other than WSI from the LIS simultaneously in a state where the WSI viewer is in an open state. Further, the pathologist can input a diagnosis report into the LIS. When the pathologist changes the case file folder on the WSI management system, the diagnosis screen of the LIS which is currently in an open state is automatically switched to a page for a changed pathology number. When the description of findings is not yet saved in the LIS, a confirmation screen for confirming whether to save the description is displayed and, thereafter, the page is moved to a page for the changed pathology number. Such a flow from the selection of the case file folder to making a report can be considered as a directional flow which is the same as the diagnosis flow that has been conventionally performed by pathologists, that is, the flow where a glass slide is set on a microscope, an image is viewed under the microscope, and a report is then made on the LIS. In contrast, in the case of a directional flow where an image is viewed by following a WSI link from the diagnosis screen of the LIS, the pathologist cannot access an image included in the case file folder unless the pathologist opens the case screen of the LIS. In other words, access to WSI, which is most important for a pathological diagnosis, requires the increased number of steps, and time lag of several tens of seconds occurs for each case. A pathologist is required to process a large number of case files in daily work and hence, such time lag may lead to a delay of a diagnosis and fatigue for the pathologist, that is, the introduction of digital pathology may cause drawbacks on the contrary. By starting work from the WSI management system, the pathologist can smoothly switch from a diagnosis using a microscope to a diagnosis using WSI and hence, it is possible to make a diagnosis more efficiently.

When making a pathological diagnosis report by the LIS is completed, a report completion notification is delivered to a clinician through the electronic medical record system that is linked with the LIS. By receiving the report completion notification, the clinician can identify the end of the pathological diagnosis and hence, the clinician can decide treatment policy, for example, by referring to the report. Even in the case where the clinician desires to view an image that is not attached to the report, the WSI link is formed in the LIS and hence, the clinician can confirm a necessary image by calling the image from the WSI management system through the WSI link. Conventionally, it is necessary for a clinician to make a request again to a pathologist to confirm an image. However, due to the linkage between the WSI management system and the LIS, a clinician can confirm an image without bothering a pathologist.

The pathology image management system (digital pathology management system) of this embodiment allows a pathologist who makes a pathological diagnosis not only to efficiently perform a task but also to extremely smoothly transmit information to a physician or a surgeon who decides a treatment method based on a pathological diagnosis.

Embodiment 2

Figure 2:
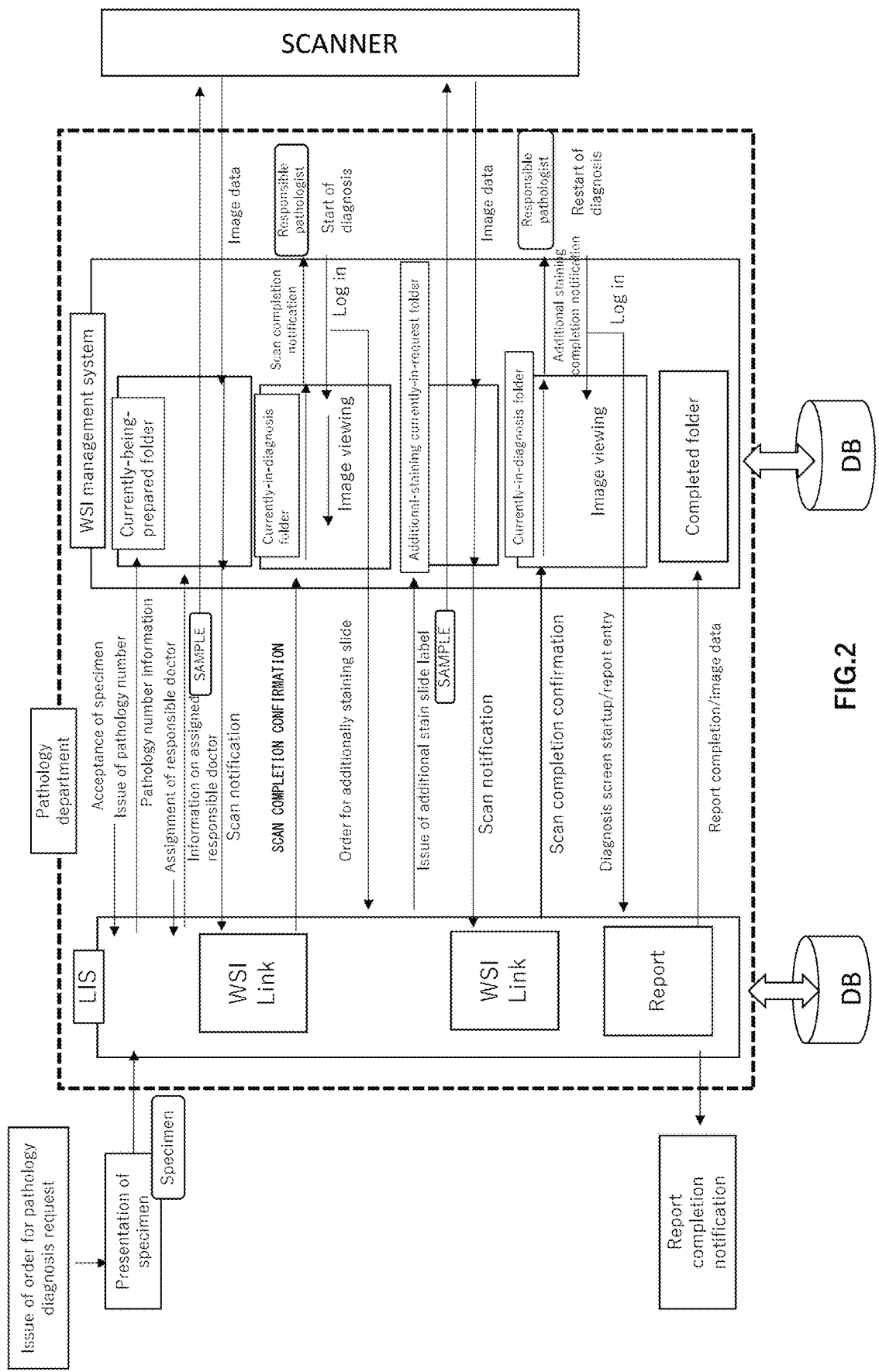
FIG. 2 is a diagram schematically showing the pathology image management system including a case where additional staining is performed.

Next, the description will be made for a case of coping with an order for additional staining (FIG. 2). When a pathological diagnosis does not reach a definitive diagnosis only with tectological information obtained by hematoxylin-eosin staining, being a basic staining method, an additional staining test that uses special staining or immunohistochemistry becomes necessary. Also in the case where additional staining becomes necessary, the LIS is linked with the WSI management system as shown in the embodiment, thus allowing efficient diagnostic work.

The step of issuing an order for a pathological diagnosis request from the clinical department, the step of preparing glass slides, and the step of a pathologist viewing an image in the case file folder stored in the currently-in-diagnosis folder are performed in the same manner as the above-mentioned embodiment 1. When the pathologist determines as a result of viewing the image that additional staining is further necessary, an order for additionally staining the slide is given via the LIS. When the order for additional staining is given, an additional stain slide label is issued and information on the order for additional staining is sent to the case file folder in the WSI management system. When the case file folder receives the order for additional staining, the case file folder is transferred to an additional-staining currently-in-request folder from the currently-in-diagnosis folder, being the place where the case file folder is currently stored.

When a glass slide, on which additional staining is performed, is prepared and is set on the scanner, image import is started. Image data read by the scanner is associated with a pathology number, and is then stored in the case file folder in the additional-staining currently-in-request folder. The WSI management system notifies the LIS of the completion of scanning for each glass slide. When the LIS receives a scan notification, a WSI link is formed. When a WSI link is formed in the LIS for each of all glass slides to which an order for additional staining is given, the scan completion notification is delivered to the WSI management system, and the case file folder is moved from the additional-staining currently-in-request folder and is stored in the currently-in-diagnosis folder. Simultaneous with such operations, an additional staining completion tag is applied to the case file folder. Although the detail will be described below, this system is built such that a necessary tag can be applied to each case file folder. A specific tag or an arbitrary tag for each pathologist can be applied, thus allowing the pathologist to easily view or search for the case file folder.

After the case file folder is stored in the currently-in-diagnosis folder and the additional staining completion tag is applied to the case file folder, the WSI management system delivers to the responsible pathologist a notification indicating the completion of additional staining. After the pathologist receives such a notification in a state of being logged in the WSI management system, when the pathologist accesses the case file folder to which the additional staining completion tag is applied, the pathologist can view added images and can confirm the completion of preparation for restarting a diagnosis. A flow after a diagnosis is restarted, that is, the flow from making a report to completion of diagnosis, is substantially equal to the corresponding flow in the embodiment 1.

As described above, even in the case where additional staining is performed, all images for each specimen are stored in a case file folder. A pathologist can complete a diagnosis by viewing all data stored in the case file folder and by viewing patient information via the LIS. Accordingly, the pathologist can make a diagnosis efficiently.

Embodiment 3

Next, the description will be made for a method for giving an alert to a responsible pathologist and a method for enabling the responsible pathologist to search for a specific case by applying tags. In making a pathological diagnosis, an urgent diagnosis may be required. For example, in the case where the condition of a patient is unstable, thus requiring treatment to be started as soon as possible, a clinician issues a pathology order while specifying necessity of an "urgent" diagnosis by the electronic medical record system, or the clinician directly makes contact with the pathology department by a means such as telephone to inform the necessity of an urgent diagnosis. For such a case having a request for an urgent diagnosis, it is necessary to make a diagnosis by priority and to make a report to the clinician as soon as possible. A tag is applied to the case that demands an urgent diagnosis and such a case is displayed on the terminal for a responsible pathologist. With such a configuration, it is possible to give an alert to the responsible pathologist.

When a clinician gives an order for pathological diagnosis request, the clinician can specify, through the electronic medical record system, that the specimen urgently requires a diagnosis report. At the point in time when an order is issued from the electronic medical record system, information that the specimen requires an urgent diagnosis is transmitted to the LIS, and the information is delivered to the WSI management system via the LIS. A tag for "urgent case" is applied to the specimen that is specified, via the electronic medical record system, as the case requiring an "urgent" diagnose. At the point in time when scanning is completed and a diagnosis is allowed, the responsible pathologist is notified of the presence of an urgent case on the terminal for the responsible pathologist. There may be a case where necessity of an urgent diagnosis for a specimen is informed via a route different from an order. In such a case, by manually applying an urgent tag to the case file folder on the WSI management system or by manually changing a priority order during scanning, it is possible to apply a tag for "high priority". For the case file folder to which such processing is applied, the responsible pathologist is notified of the presence of an urgent case on the terminal for the responsible pathologist at the point in time when scanning is completed and diagnosis is allowed.

Figure 3:
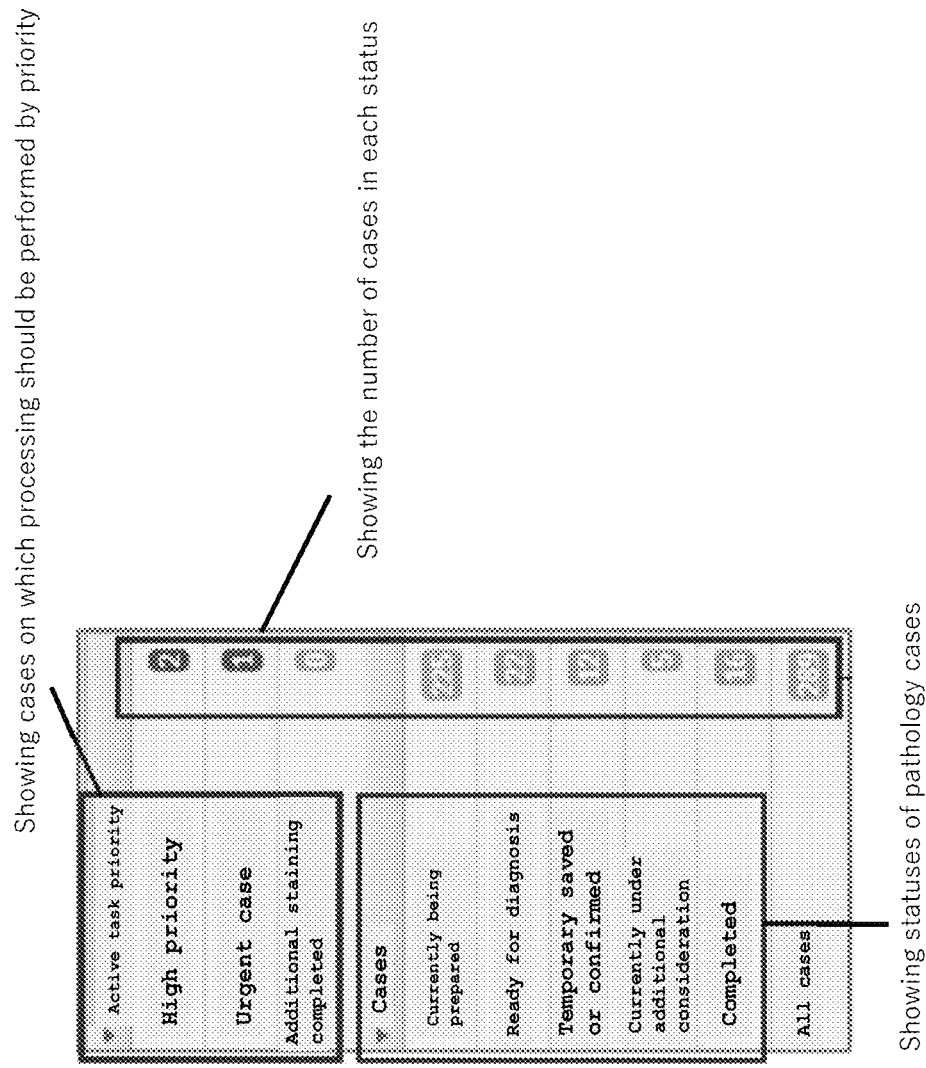
FIG. 3 shows an example of a screen showing case statuses.

FIG. 3 shows a list of case statuses confirmed on the WSI management system terminal for the responsible pathologist. FIG. 3 shows that the responsible pathologist has two specimens in the status "high priority" and one specimen in the status "urgent case". The status "high priority" is obtained when a priority order of scanning is changed due to reception of information on necessity of an urgent diagnosis. The status "urgent case" is obtained when an urgent diagnosis is designated by the clinician through the electronic medical record system or when a tag for an urgent case is manually applied to the specimen. A pathologist can grasp, in the form of a list, statuses of cases for which the pathologist is responsible, such as a case in the state "currently being prepared" and a case in the status "ready for diagnosis" where a diagnosis is allowed. As a result, the pathologist can understand specimens on which processing should be performed by priority and can grasp the statuses of respective specimens and hence, the pathologist can efficiently perform a diagnosis while taking into account the priority order.

A case in the status "currently being prepared" indicates a case where a pathologist is not allowed to start a diagnosis yet due to incompletion of scanning, but the case is assigned to the pathologist. FIG. 3 shows that 225 cases are in the status "currently being prepared".

The status "ready for diagnosis" indicates a state where scanning is completed for all glass slides of the case, so that a pathologist is allowed to start a diagnosis. When scanning is completed, the status of each case file folder is changed from "currently being prepared" to "ready for diagnosis", thus allowing the pathologist to perform work sequentially without waiting for the completion of scanning for all cases to which the pathologist is assigned as a responsible pathologist for a diagnosis. In conventional specifications, information on the scan completion notification is not displayed on the WSI management system and hence, the pathologist is required to confirm the number of glass slides and a kind of staining from specimen information in the LIS. With specifications of the present invention, the pathologist can determine that a diagnosis is allowed to start at any time for a case in the status "ready for diagnosis".

The status "temporarily saved or confirmed" indicates that a pathologist has entered findings on a diagnosis creation screen of the LIS and has performed either the operation of temporarily saved or confirmed. The status in the WSI management system shifts from the status "ready for diagnosis" to the status "temporarily saved or confirmed", and the pathologist can confirm in real time the state of reduction in the number of cases that are not yet started.

There may be a case where an inexperienced pathologist requests other pathologist to check a diagnosis. In such a case, at a stage where a temporary report is made, the inexperienced pathologist can temporarily save the temporary report and can designate other pathologist to whom the inexperienced pathologist desires to make an evaluation request. Specifically, a person who makes an evaluation request selects, for each case folder, a pathologist, to whom the person desires to make an evaluation request, to add the pathologist as an evaluator. When the pathologist is selected as an evaluator, the pathologist is assigned as the evaluator, and the case file folder that is requested to evaluate is displayed in the status column "temporarily saved or confirmed" in the case list of the evaluator. When the evaluator logs in the system with own ID, the evaluator can view and confirm images to check the diagnosis in the case folder that the evaluator is requested to evaluate.

In the case where an additional staining test becomes necessary in the course of a diagnosis, an additional order is submitted from the LIS and, at the point in time when such an order is accepted, information is sent to the WSI management system and the status shifts to "currently under additional consideration". With such a configuration, even when a large number of additional tests are done, the results can be confirmed and reported without being overlooked. Further, there may be a case of an error occurring where an order is issued on the LIS but is not received. For example, the following human error may occur. When a large number of orders are made simultaneously, the person making the orders forgets to perform a sending operation after the order is issued. Alternatively, the receiver of the order forgets to perform an order execution operation. Also in such cases, the status does not shift on the WSI management system and hence, the person can realize such an error. After the completion of scanning for glass slides in the additional test for which an order is made, the "additional staining completion tag" is applied to the case, and the case is displayed in the column of the priority list (active task priority) on the WSI management system to notify the pathologist of the completion. With such a configuration, it is possible to prevent the pathologist from forgetting to confirm the case and it is also possible to rapidly report the result of the additional test.

After a diagnosis report of the case is completed in the LIS, if the case has no necessity of an additional report, the status of the case will shift to "completed". The pathologist can visually perceive not only the number of completed works but also a sense of achievement and hence, a psychological load of the pathologist with respect to work may reduce.

Each of the case status "currently being prepared", "ready for diagnosis", "temporarily saved or confirmed", "currently under additional consideration", and "completed" indicates that a specimen is in the above-mentioned state. Such case statuses can be changed according to the actual situation of each hospital. Since the operation of the WSI management system and the operation of the LIS are synchronized, a time period necessary for the case file folder to shift between these statuses is substantially zero or is equal to or less than several seconds. Accordingly, there is no possibility of giving a stress to a user.

In the case where the pathologist desires to have a consultation with other pathologist about the responsible case, the pathologist can ask for other specialist's opinion by applying a tag indicating that the pathologist desires to have a consultation. A tag can also be applied an interesting case, for example, so as to allow the pathologist to search for a case necessary for study. An arbitrary tag can be applied to each case and hence, it is also possible to efficiently utilize the system for communication with other specialist or for case study.

The WSI management system may also additionally have a function that allows a search without applying a tag. For example, it is sufficient to build a system where, by inputting one or more items in a search window of the WSI management system, the names of corresponding folders can be saved in the WSI management system in the form of a list. Examples of the items include the name of organ (lung, stomach, large intestine, mammary gland, or the like), the name of a department (respiratory surgery, gastroenterology, department of hematology or the like), a collection date (designate corresponding date or range), specimen classification (biopsy, surgical, urgent, other hospital, and the like), and the name of diagnostician. Specimen information is saved in the WSI in the form of structure, thus allowing a detailed search.

For a further detailed search, it is sufficient to build the following system. When a list of cases for which a search is made in the LIS is exported to the WSI management system, a tag having the same name as the case list is applied to each file having a corresponding pathology number, and a person who made the list is allowed to view and manage the files. Further, if a tag for public disclosure can be applied to a case list to allow other people to view the case list, the case list can contribute when pathologists make a case study or give training, for example. When linkage of data is formed between the LIS and the WSI management system to allow collective operation of applying tags, also in the WSI management system, to the list exported from the LIS, a smooth operation can be achieved.

Embodiment 4

The description will be made for an archive system where data with low access frequency are moved to a storage for storing data and the data can be retrieved when necessary. After a diagnosis ends and report is completed, image data are accumulated in a completed folder. The accumulation of images reduces the storage capacity of the WSI management system, thus causing a reduction in access speed. For this reason, it is necessary to build a system that can ensure a space in a storage.

Figure 4:
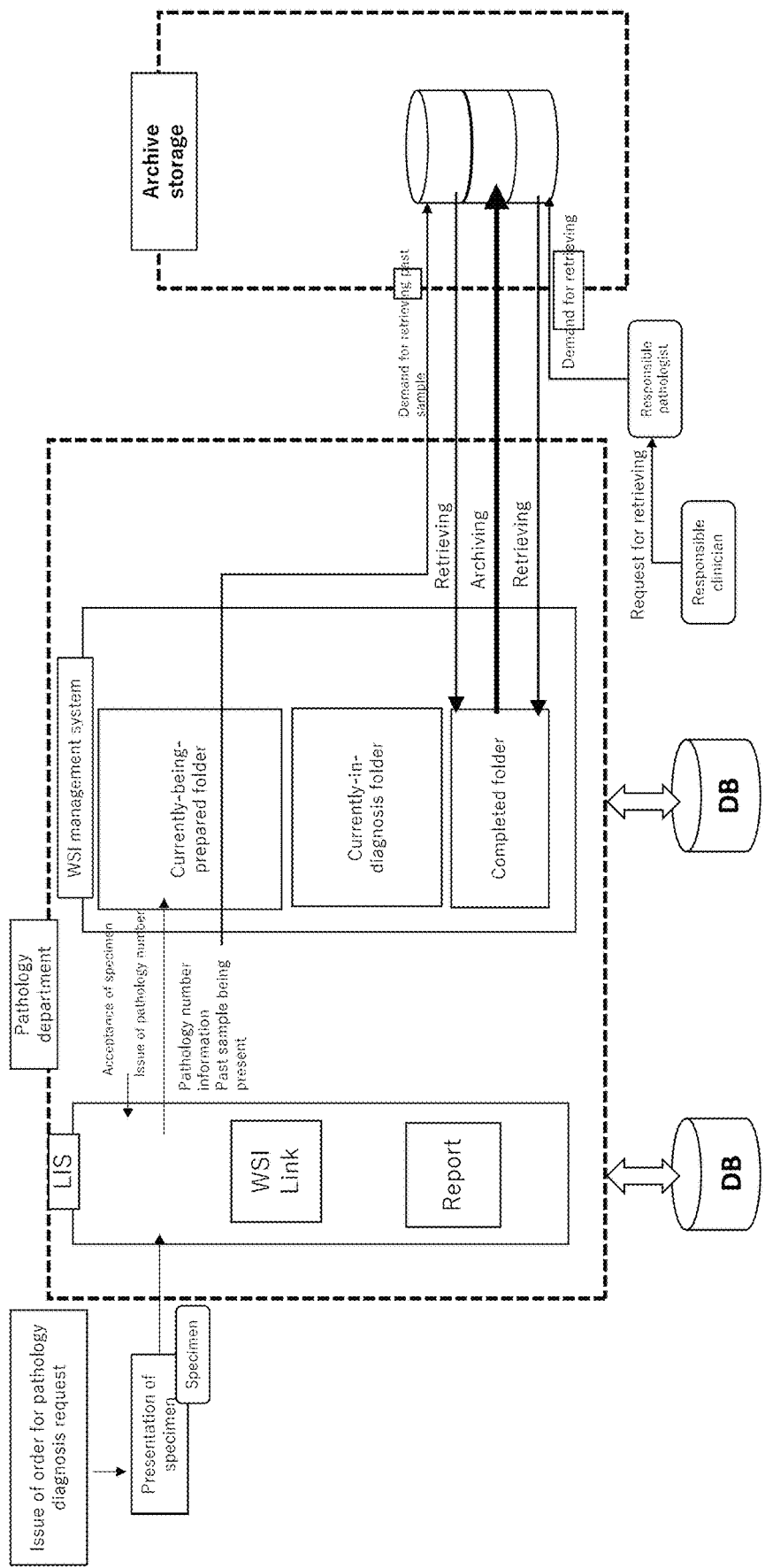
FIG. 4 is a diagram schematically showing archiving and retrieving of data.

A pathologist requires high speed access for a case with high access frequency, such as a case currently in diagnosis or a case immediately after diagnosis. To ensure high speed access, it is necessary to ensure a space in an online storage. Therefore, a configuration is adopted where, after a lapse of a predetermined time period from the completion of report, the case is stored in an archive storage to ensure a space in the online storage (FIG. 4).

After the report is made, that is, after a lapse of a predetermined time period from the movement of the case file to the completed folder, the case file is automatically moved to the archive storage to ensure a space in the online storage. A timing at which the case file is moved to the archive storage after the completion of report varies according to the number of pathological diagnosis cases of each facility and the storage capacity and hence, it is sufficient to suitably decide a timing for each facility. For example, the case file is moved to the completed folder and, thereafter, after a lapse of three months, the case file is automatically moved to the archive storage. It is sufficient to program a system such that a period is decided by taking into account an access frequency of a responsible pathologist, a storage capacity, and the like, and the case file is moved after the decided period. Archiving involves the movement of large capacity data. Therefore, when the system is programmed such that archiving starts within a timeframe with not many users, that is, outside business hours, work is not obstructed. For example, when the system is programmed such that archiving starts after the date changes after a lapse of three months, that is, from midnight of the next day after a lapse of three months, it is possible to move data to the archive storage without obstructing work.

Even when the case file is moved to the completed folder due to the completion of the report, for a case that can be anticipated to be viewed for the purpose of study or education, access can be anticipated even after a lapse of the time period. By applying a tag for exclusion from archiving to such a folder, it is possible to prevent such a folder from being moved to the archive storage. The case file to which the tag for exclusion from archiving is applied is not moved from the online storage even after a lapse of three months and hence, high speed access to such a case file can be achieved.

There may be a case where when a specimen is newly accepted for a case and a pathology number is issued, the case has past samples. In such a case, it is necessary to refer to the past samples. Therefore, at a stage where the specimen is newly accepted and the pathology number is applied to the specimen, when the case has past samples, all past samples are retrieved. Also in the case of giving an additional order for a case stored in the archive, retrieving is performed. The past samples are retrieved to the completed folder. To inform that the past samples are retrieved data, a tag such as "already retrieved" is applied to each of the past samples. Such a tag informs that consideration is already given to the data.

Both archiving and retrieving involve the movement of large capacity data, thus imposing a load on a network. Therefore, it is preferable to set both archiving and retrieving to be performed outside business hours. Even outside the business hours, it is not preferable to perform archiving and retrieving simultaneously from a viewpoint of a load imposed on the network. It is preferable to set a start time for archiving to a time different from the start time for retrieving. For example, when archiving is set to start from midnight as described above, retrieving is set to start from 10 PM or from 4 AM at which archiving is expected to end.

The system is set such that, in the case where a past specimen is retrieved, after a lapse of a predetermined period of time from retrieving, the past specimen is archived. The past specimen is used as a reference for a case of a new diagnosis and hence, the system may be set such that the past specimen is archived after a shorter period than data of the new specimen. For example, assume that the system is set such that data for a new diagnosis is archived after a lapse of three months. In such a case, the system may be set such that the retrieved case file is archived after two months. Start time for archiving, start time for retrieving, and a period required before data are moved from the completed folder to the archive storage may be set according to the actual situation of each facility.

The system is set such that, in the case where the responsible pathologist desires again to refer to data moved to the archive storage, the responsible pathologist can manually retrieve the data from the archive storage. The responsible clinician can also retrieve the case file from the archive storage via the responsible pathologist.

Figure 5:
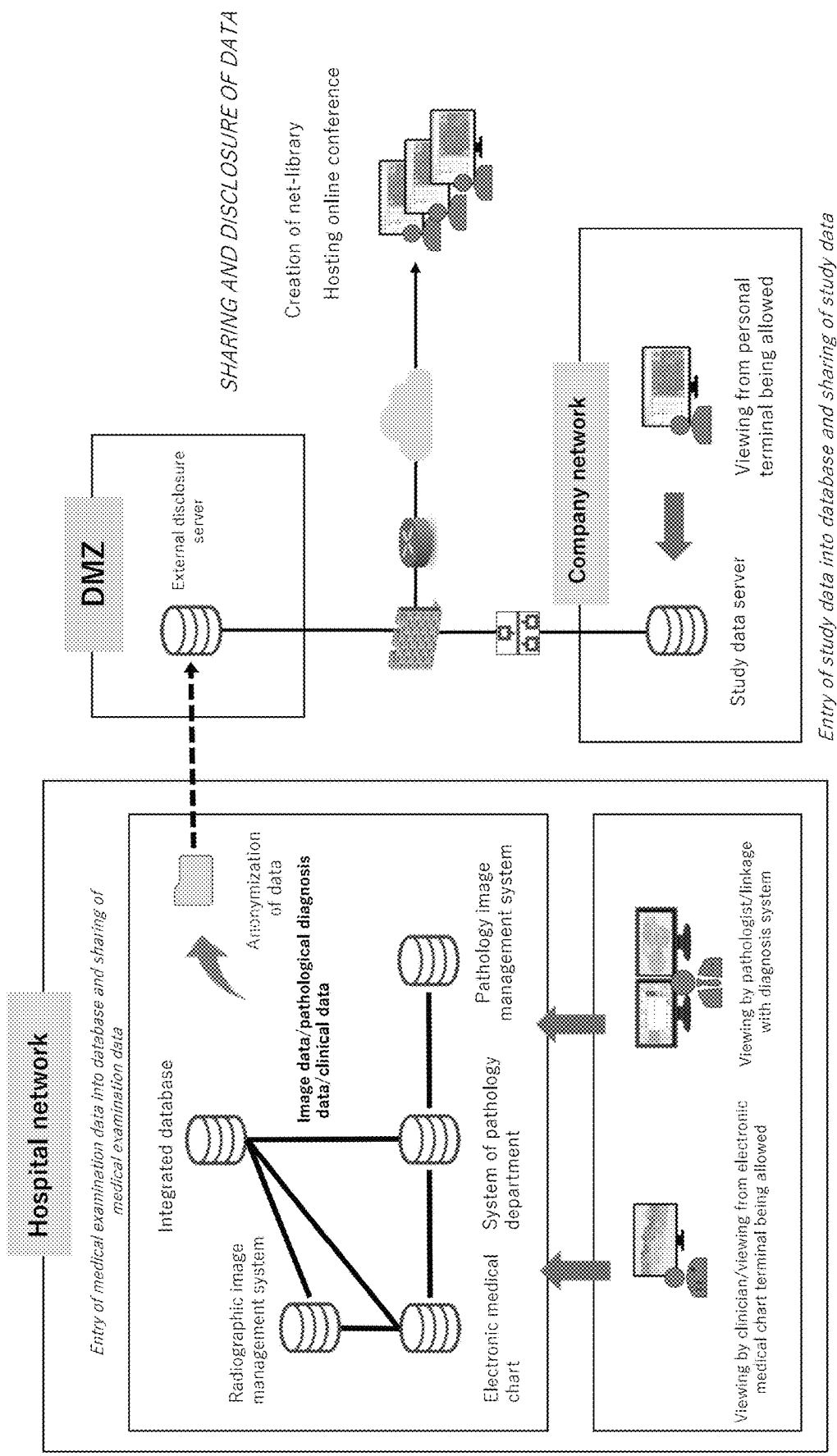
FIG. 5 is a diagram schematically showing the relationship between a system of a pathology department and other systems in a hospital, a company network, and data sharing with outside.
Figure 6:
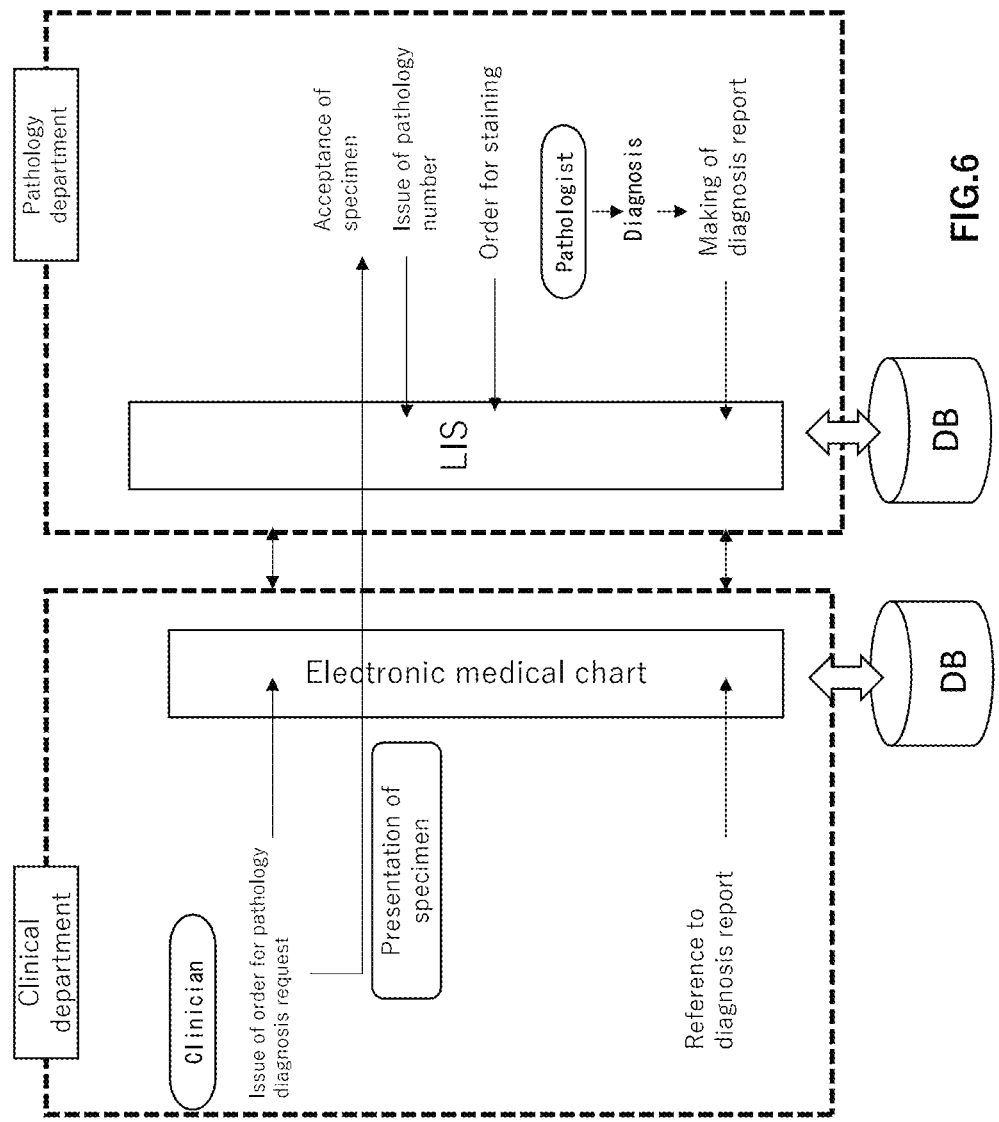
FIG. 6 is a diagram schematically showing a linkage between an electronic medical record system of a clinical department and an LIS of the pathology department before a WSI is introduced.
Figure 7:
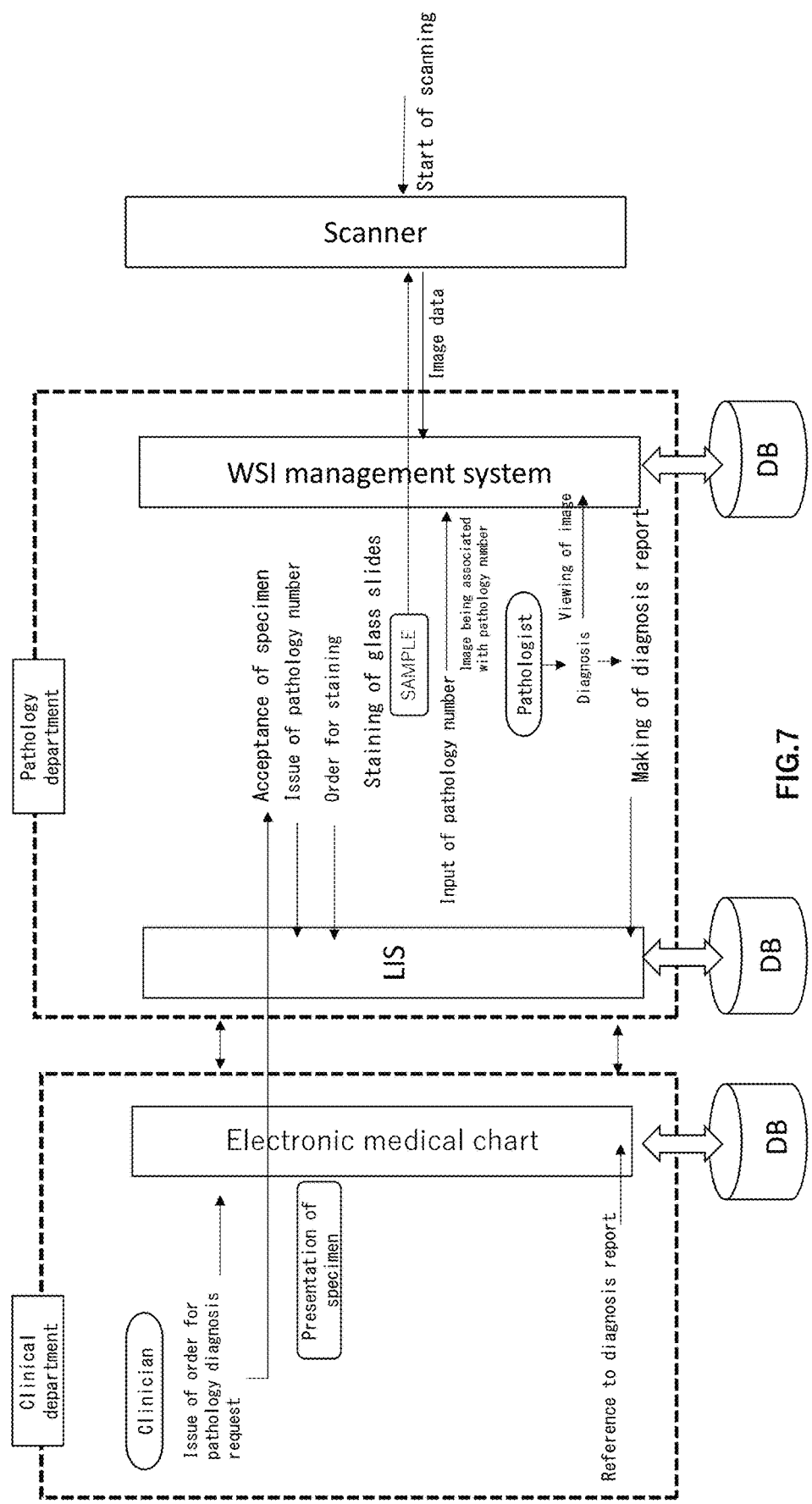
FIG. 7 is a diagram schematically showing a conventional linkage between the electronic medical record system of the clinical department and the LIS of the pathology department after the WSI is introduced.

Next, the description will be made for the system of the pathology department and other system in a hospital, a company network, and data sharing with outside (FIG. 5). A hospital network system is built such that data can be viewed through an integrated database or the electronic medical record. However, a hospital network is set as a closed network environment to prevent leakage of information on an individual patient to the outside. The network system is set such that, when a clinician views pathological diagnosis data or data of a diagnosis made by another doctor, such as radiographic image diagnosis data, the clinician can view the data only from an electronic medical record terminal. The network system is built such that although a pathologist can also view not only pathology images but also other data necessary for a diagnosis from the electronic medical record system, the pathologist can view such images and data only from a terminal connected to the hospital network. In making a diagnosis, a pathologist or a clinician can access the system in the hospital and view data to make a diagnosis. In other words, the network is built such that even a pathologist or a clinician cannot view data for the purpose of study or the like.

In the case of accessing similar case for which another doctor is responsible in order to use the data for the purpose other than a diagnosis, for example, for the purpose of the responsible doctor sharing information with another doctor in a hospital or for the purpose of study or the like, the similar case can be viewed from the company network through a study data server. The system is built such that, even within a hospital, in the case of viewing data from outside the hospital network for the purpose other than diagnosis, all data are anonymized. Accordingly, in the case of viewing data by accessing the study data server from a personal terminal through the company network to perform an analysis for the purpose of study, data are anonymized and hence, it is not necessary to be concerned about leakage of the personal information of patients.

Further, for creating a net-library or for hosting an online conference, for example, information may be shared with medical personnel outside a hospital or data may be disclosed. In such a case, it is sufficient to set the system such that required data are saved in an external disclosure server in a demilitarized zone (DMZ) and access to the data from the outside is allowed to allow data sharing. With such a configuration, access from the outside is limited to data in the DMZ, and it is possible to prevent access to data in the hospital.

The system building described above can be suitably changed according to the actual situation of each organization provided that the purpose is not changed. In the system of the pathology department, system design in the form following the conventional workflow of pathologists not only allows a pathologist to make a diagnosis smoothly but also allows a clinician to save effort, thus contributing to a rapid diagnosis.

The invention claimed is:

1. A pathology image management system that controls linkage among a scanner, a whole slide image (WSI) management system, and a laboratory information system (LIS), the scanner scanning a glass slide to digitize the glass slide, wherein
WSI data obtained by the scanner are transferred to the WSI management system,
the WSI management system delivers a scan notification to the LIS, the scan notification notifying that the WSI data is transferred, and
a WSI link is formed in the LIS that receives the scan notification.

2. The pathology image management system according to claim 1, wherein
the WSI management system includes
a currently-being-prepared folder that stores information on the glass slide up to a point before formation of the WSI link,
a currently-in-diagnosis folder that stores the WSI data in a state where viewing of an image is allowed, and
a completed folder that stores the WSI data for which a report is made.

3. The pathology image management system according to claim 2, wherein
the WSI management system further includes an additional-staining currently-in-request folder.

4. The pathology image management system according to claim 2, wherein
upon acceptance of a specimen, the LIS issues a pathology number,
the pathology number issued is stored in the currently-being-prepared folder of the WSI management system, and
the pathology number issued is printed on the glass slide or is stuck to the glass slide in a form of a label,
the scanner simultaneously reads the WSI data and the pathology number printed or stuck in the form of the label to cause the pathology number to be associated with the WSI data, and
the pathology number and the WSI data are stored in the currently-being-prepared folder of the WSI management system.

5. The pathology image management system according to claim 2, wherein
a link is formed for WSI in response to scan notification,
after the LIS confirms completion of scanning for each of all glass slides for which an order is made,
a case file folder is moved from the currently-being-prepared folder and is stored in the currently-in-diagnosis folder, and
a scan completion notification is sent to a responsible doctor.

6. The pathology image management system according to claim 2, wherein
upon determination of necessity of additional staining,
an order for the additional staining is given to the LIS, so that an additional stain slide label is issued or the pathology number is printed on the glass slide,
the scanner obtains an image of the glass slide on which required staining is performed,
WSI data on the glass slide on which the additional staining is performed are transferred to the WSI management system, the WSI data being obtained by the scanner,
the WSI management system delivers, to the LIS, the scan notification notifying that the WSI data are transferred, and
a WSI link of an additional staining image is formed in the LIS that receives the scan notification.

7. The pathology image management system according to claim 2, wherein
after a diagnosis report is made in the LIS,
the WSI data are moved from the currently-in-diagnosis folder and are stored in the completed folder.

8. The pathology image management system according to claim 2, comprising an archive storage for storing data, wherein
the pathology image management system is built such that a case file folder stored in the completed folder is automatically moved to the archive storage after a lapse of a predetermined period of time.

9. The pathology image management system according to claim 8, wherein in a case where a specimen that is newly accepted has a past sample,
the LIS detects presence of the past sample, and retrieving of the past sample from the archive storage is demanded, and the past sample is automatically retrieved.

10. The pathology image management system according to claim 8, wherein a tag is applied to the case file folder that is retrieved from the archive storage, and
the case file folder is stored in the archive storage again after a lapse of a predetermined period of time.

11. The pathology image management system according to claim 1, wherein
the WSI data in which the WSI link is formed
are saved in a case file folder for every one specimen, and
are stored in a folder in the WSI management system.

12. The pathology image management system according to claim 1, wherein a tag applied through the LIS is displayed on a terminal for a responsible pathologist, the tag showing a priority order of diagnosis.

13. The pathology image management system according to claim 1, wherein application of an arbitrary tag is allowed to be applied by a terminal for a responsible pathologist.

* * * * *